United States Patent

Sauter et al.

Patent Number: 5,399,579
Date of Patent: Mar. 21, 1995

[54] FUNGICIDAL COMPOSITIONS

[75] Inventors: Hubert Sauter, Mannheim; Klaus Schelberger, Goennheim; Reinhold Saur, Boehl-Iggelheim; Gisela Lorenz, Neustadt; Eberhard Ammermann, Heppenheim, all of Germany

[73] Assignee: BASF Aktiengesellschaft, Ludwigshafen, Germany

[21] Appl. No.: 188,012

[22] Filed: Jan. 28, 1994

Related U.S. Application Data

[62] Division of Ser. No. 87,317, Jul. 8, 1993, Pat. No. 5,317,027, which is a division of Ser. No. 943,677, Sep. 11, 1992, Pat. No. 5,260,326.

[30] Foreign Application Priority Data

Sep. 12, 1991 [DE] Germany ............... 41 30 298.2

[51] Int. Cl.⁶ ................ A01N 37/12; A01N 37/44; A01N 43/64
[52] U.S. Cl. ..................... 514/383; 514/539
[58] Field of Search .................. 514/383, 539

[56] References Cited

U.S. PATENT DOCUMENTS

| | | | |
|---|---|---|---|
| 4,829,085 | 5/1989 | Wenderoth et al. | 514/522 |
| 5,059,616 | 10/1991 | Dutzmann et al. | 514/383 |
| 5,106,848 | 4/1992 | Seele et al. | 514/239.5 |

*Primary Examiner*—Allen J. Robinson
*Attorney, Agent, or Firm*—Oblon, Spivak, McClelland, Maier & Neustadt

[57] ABSTRACT

Fungicidal compositions consisting of
a) methyl α-methoximino-2-[2-methylphenoxy)-methyl]-phenylacetate

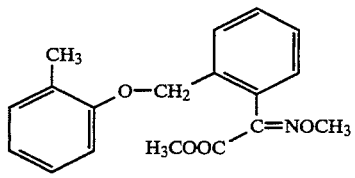

and
b) an azole active ingredient selected from the following group:
(Z)-2-(1,2,4-triazol-1-ylmethyl)-2-(4-fluorophenyl)-3-(2-chlorophenyl)-oxirane of the formula

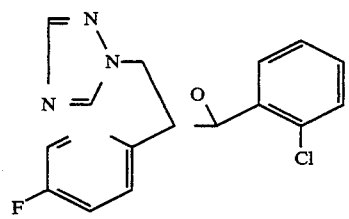

1-butyl-1-(2,4-dichlorophenyl)-2-(1,2,4-triazol-1-yl)-ethanol (common name hexaconazole), 1-[(2-chlorophenyl)methyl]-1-(1,1-dimethyl)-2-(1,2,4-triazol-1-yl-ethanol, 1-(4-fluorophenyl)-1-(2-fluorophenyl)-2-(1,2,4-triazol-1-yl)-ethanol (common name flutriafol), (RS)-4-(4-chlorophenyl)-2-phenyl-2-(1H-1,2,4-triazol-1-ylmethyl)-butyronitrile, 1-[(2 RS, 4 RS; 2 RS, 4 SR)-4-bromo-2-(2,4-dichlorophenyl)-tetrahydrofurfuryl]-1H-1,2,4-triazole, 3-(2,4-dichlorophenyl)-2-(1H-1,2,4-triazol-1-yl)-quinazolin-4(3H)-one, (RS)-2,2-dimethyl-3-(2-chlorobenzyl)-4-(1H-1,2,4-triazol-1-yl)-butan-3-ol, bitutanol, triadimefon, triadimenol, cyproconazole, dichlobutrazol, difenoconazole, diniconazole, etaconazole, propiconazole, flusilazole, tebuconazole, imazalil, penconazole, prochloraz, tetraconazole and salts of such azole active ingredients, and methods of combating fungi with such compositions.

2 Claims, No Drawings

FUNGICIDAL COMPOSITIONS

This is a division of application Ser. No. 08/087,317, filed on Jul. 8, 1993, now U.S. Pat. No. 5,317,027, which is a divisional of Ser. No. 07/943,677, filed Sep. 11, 1992, now U.S. Pat. No. 5,260,326.

The present invention relates to fungicidal compositions having a synergistic fungicidal action, and methods of combating fungi with these compositions.

It is known to use methyl α-methoximino-2-[2-methylphenoxy)-methyl]phenylacetate

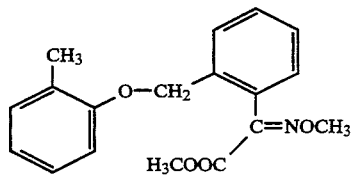

as a fungicide (EP 253 213). It is also known to use an azole active ingredient selected from the following group: (Z)-2-(1,2,4-triazol-1-ylmethyl)-2-(4-fluorophenyl)-3-(2-chlorophenyl)-oxirane of the formula

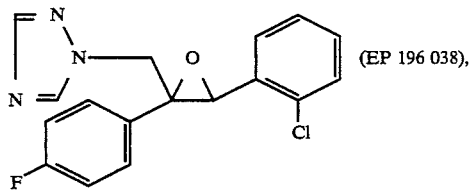

(EP 196 038), 1-butyl-1-(2,4-dichlorophenyl) -2-(1,2,4-triazol-1-yl)-ethanol (common name hexaconazole, 1-[(2-chlorophenyl)methyl]-1-(1,1-dimethyl)-2-(1,2,4-triazol-1-yl-ethanol, 1-(4-fluorophenyl)-1-(2-fluorophenyl)-2-(1,2,4-triazol-1-yl)-ethanol (common name flutriafol), (RS)-4-(4-chlorophenyl)-2-phenyl-2-(1H-1,2,4-triazol-1-ylmethyl)-butyronitrile, 1-[(2 RS, 4 RS; 2 RS, 4 SR)-4-bromo-2-(2,4-dichlorophenyl)-tetrahydrofurfuryl]-1H-1,2,4-triazole, 3-(2,4-dichlophenyl)-2-(1H-1,2,4-triazol-1-yl)-quinazolin-4(3H)-one, (RS)-2,2-dimethyl-3-(2-chlorobenzyl)-4-(1H-1,2,4-triazol-1-yl)-butan-3-ol, bitertanol, triadimefon, triadimenol, cyproconazole, dichlobutrazol, difenoconazole, diniconazole, etaconazole, propiconazole, flusilazole, tebuconazole, imazalil, penconazole, prochloraz, tetraconazole, or a salt of such an azole active ingredient, as fungicide.

We have now found that a composition of
a) methyl α-methoximino-2-[2-methylphenoxy)-methyl]-phenylacerate

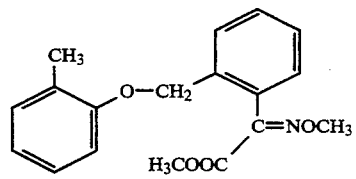

and
b) an azole active ingredient selected from the following group:

(Z)-2-(1,2,4-triazol-1-ylmethyl)-2-(4-fluorophenyl)-3-(2-chlorophenyl)-oxirane of the formula

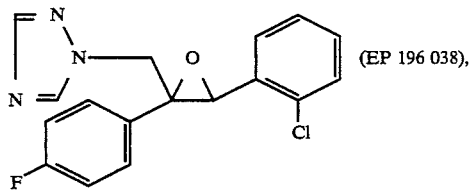

1-butyl-1-(2,4-dichlorophenyl)-2-(1,2,4-triazol-1-yl)-ethanol (common name hexaconazole), 1-[(2-chlorophenyl)methyl]-1-(1,1-dimethyl)-2-(1,2,4-triazol-1-yl-ethanol, 1-(4-fluorophenyl)-1-(2-fluorophenyl)-2-(1,2,4-triazol-1-yl)-ethanol (common name flutriafol), (RS)-4-(4-chlorophenyl)-2 -phenyl-2-(1H-1,2,4-triazol-1-ylmethyl)butyronitrile, 1-[(2 RS, 4 RS; 2 RS, 4 SR)-4-bromo-2-(2,4-dichlorophenyl)-tetrahydrofurfuryl]-1H-1,2,4-triazole, 3-(2,4-dichlorophenyl)-2-(1H-1,2,4-triazol-1-yl)-quinazolin-4(3H)-one, (RS)-2,2-dimethyl-3-(2-chlorobenzyl)-4-(1H-1,2,4-triazol-1-yl)-butan-3-ol, bitertanol, triadimefon, triadimenol, cyproconazole, dichlobutrazol, difenoconazole, diniconazole, etaconazole, propiconazole, flusilazole, tebuconazole, imazalil, penconazole, prochloraz, tetraconazole and salts of such azole active ingredients, have a synergistic fungicidal action.

The weight ratio of a):b) is selected to give a synergistic fungicidal action, for example 10:1 to 1:10, especially 5:1 to 1:5, and preferably 3:1 to 1:3. The synergistic action of the composition is apparent from the fact that the fungicidal action of the composition of a)+b) is greater than the sum of the fungicidal actions of a) and b).

With regard to the —C=N— double bond, component a) may be present in two stereoisomeric forms. The (E)-isomer is preferred.

The invention embraces compositions containing both the pure isomers of compound a), especially the (E)-isomer, and compositions containing mixtures of isomers.

Preferred compositions are those containing component a) predominantly in the form of the (E)-isomer.

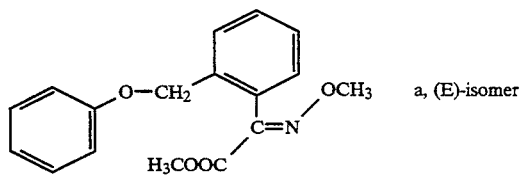

a, (E)-isomer

The azole active ingredients b) may also be present in the form of their salts. These compositions too are encompassed by the invention.

Salts are prepared by reaction with acids, e.g., hydrohalo acids such as hydrofluoric acid, hydrochloric acid, hydrobromic acid and hydroiodic acid, or sulfuric acid, phosphoric acid or nitric acid, or organic acids such as acetic acid, trifluoroacetic acid, trichloroacetic acid, propionic acid, glycolic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid and 1,2-naphthalenedisulfonic acid.

In practice, it is advantageous to use the pure active ingredients a) and b), to which further active ingredients such as insecticides, acaricides, nematicides, herbicides, further fungicides, growth regulators and/or fertilizers may be added.

The fungicidal compounds according to the invention may be applied for instance in the form off directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

Normally, the planes are sprayed or dusted with the active ingredients, or the seeds of the plants are treated with the active ingredients.

The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and methylcellulose.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation produces of naphthalene or naphthalenesulfonic acids with thenol and formaldehyde, polyoxyethylene octylthenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable produces such as grain meals, bark meal, wood meal, and nutshell meal, cellulosic powders, etc.

The novel compounds are extremely effective on a broad spectrum of phytopathogenic fungi, in particular from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The compounds are applied by treating the fungi or the seeds, plants or materials threatened by fungus attack, or the soil with a fungicidally effective amount of the active ingredients.

The agents may be applied before or after infection of the materials, plants or seeds by the fungi.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia species in cotton and lawns,
Ustilago species in cereals and sugarcane,
*Venturia inaequalis* (scab) in apples,
Helminthosporium species in cereals,
*Septoria nodorum* in wheat,
*Botrytis citetea* (gray mold) in strawberries and grapes,
*Cercospora arachidicoia* in groundnuts,
*Pseudocercosporella herpotrichoides* in wheat and barley,
*Pyricuiaria oryzae* in rice,
*Phytophthora infestans* in potatoes and tomatoes,
Fusarium and Verticillium species in various plants,
*Plasmopara viticola* in grapes,
Alternaria species in fruit and vegetables.

The novel compounds may also be used for protecting materials (timber), e.g., against *Paecilomyces variotii.*

The fungicidal agents generally contain from 0.1 to 95, and preferably from 0.5 to 90, wt % of active ingredient.

The application rates depend on the type of effect desired, and range from 0.02 to 3 kg of active ingredient per hectare.

When the active ingredients are used for treating seed, rates of 0.001 to 50, and preferably from 0.01 to 10, g per kg of seed are generally sufficient.

Eradicative action on wheat mildew

Wheat plants of the "Kanzler" variety were treated, after 3 leaves had grown, in one experiment with wheat mildew (*Erysiphe graminis* var. tritici) resistant to fungicides containing a triazole radical in the molecule, and in a further experiment with wheat mildew sensitive to fungicides containing a triazole radical in the molecule. After the spread of fungus attack on 5% of the leaf surface the plants were treated with aqueous formulations of the active ingredients in the concentrations given. The amount of water corresponded to 400 l/ha. The plants were cultivated in the greenhouse for 20 days at 18° to 22° C.

The leaf area under fungus attack was then assessed in percent. These figures were then converted into degrees of action. The degree of action in the untreated control was set at 0. The degree of action when 0% of the leaf area was attacked by fungus was set at 100. The expected degrees ° action of the active ingredient composition were determined in accordance with the Colby formula (Colby, S. R., "Calculating synergistic and antagonistic responses of herbicide combinations", Weeds, 15, pp. 20–22, 1967) and compared with the degrees of action observed.

The values for the fungicidal action varied between the individual experiments because the plants in the individual experiments exhibited varying degrees of attack; for this reason, only the results within the same experiment can be compared with each other.

Colby formula $E = x + y - \frac{x \cdot y}{100}$

E = expected degree of action, expressed in % of the untreated control, when active ingredients A and B are used in concentrations of m and n X = degree of action, expressed in % of the untreated control, when active ingredient A is used in a concentration of m Y = degree of action, expressed in % of the untreated control, when active ingredient B is used in a concentration of n The following compounds were used for the experiments:

I. methyl a-methoximino-2-[2-methylphenoxymethyl]phenylacetate

II. (Z)-2-(1,2,4-triazol-1-ylmethyl)-2-(4-fluorophenyl)-3-(2-chlorophenyl)-oxirane III. tebuconazol (RS)-1-(4-chlorophenyl)-4,4-dimethyl-3-(1H-1,2,4-triazol-1-ylmethyl)-pentan-3-ol

EXP. 1

*Erysiphe graminis* test (wheat)—eradicative;
*Erysiphe graminis* triazole-resistant

| Active ingredient | Active ingredient concentration in spray liquor in % | Degree of action in % of untreated control |
|---|---|---|
| Control (untreated) | — | 0 |
| I. (prior art active ingredient) | 0.05 | 46 |
| II. (prior art active ingredient) | 0.05 | 18 |
| III. Tebuconazol (prior art) | 0.05 | 14 |
| Composition according to the invention | | |
| I. + II. Ratio 1:3  0.01 + 0.03 | | 75 |
| I. + III. Ratio 1:3  0.01 + 0.03 | | 80 |

The results show that 0.04% (0.01+0.03) of the composition has a better fungicidal action than 0.05% of the individual active ingredients.

The same experiment carried out with triazole-sensitive *Erysiphe graminis* confirmed the above results.

EXP. 2

*Erysiphe graminis* test (wheat)—eradicative;
*Erysiphe graminis* triazole-sensitive

| Active ingredient | Active ingredient concentration in the spray liquor in % | Degree of action in % of the untreated control |
|---|---|---|
| Control (untreated) | — | 0 |
| I. (prior art active ingredient) | 0.1 | 68 |
| | 0.01 | 24 |
| II. (prior art active ingredient) | 0.1 | 37 |
| | 0.01 | 9 |
| III. Tebuconazol prior art) | 0.1 | 35 |
| | 0.01 | 8 |
| Composition according to the invention | Degree of action observed | Degree of action calculated*) |
| I + II   0.01 + 0.01 ratio 1:1 | 51 | 30.8 |
| I + II   0.1 + 0.1 ratio 1:1 | 100 | 79.8 |
| I + II   0.1 + 0.01 ratio 10:1 | 85 | 70.8 |
| I + II   0.01 + 0.1 ratio 1:10 | 74 | 52.1 |
| I + III  0.01 + 0.01 ratio 1:1 | 49 | 30.1 |
| I + III  0.1 + 0.1 ratio 1:1 | 100 | 79.2 |
| I + III  0.1 + 0.01 ratio 10:1 | 86 | 70.5 |
| I + III  0.01 + 0.1 ratio 1:10 | 71 | 50.6 |

*)calculated according to the Colby formula

The results show that the degrees of action observed are better than the degrees of action calculated according Colby.

The same experiment carried out with triazole-sensitive *Erysiphe graminis* confirmed the above results.

We claim:

1. A fungicidal composition comprising a synergistically fungicidally effective amount of a mixture of a
   a) methyl a-methoximino-2-[2-methylphenoxy)-methyl]-phenylacetate

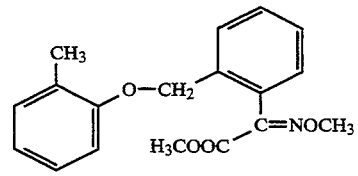

and
   b) tebuconazole or salts thereof,
wherein compounds a) and b) are present in a weight ratio of 10:1 to 1:10.

2. A process for combatting fungi, comprising applying to plants or seeds a fungicidal composition comprising a synergistically fungicidally effective amount of a mixture of:
   a) methyl a-methoximino-2-[2-methylphenoxy)-methyl]-phenylacetate

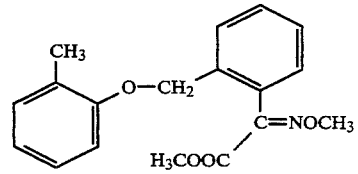

and
   b) tebuconazole or salts thereof,
wherein compounds a) and b) are present in a weight ratio of 10:1 to 1:10.

* * * * *